United States Patent
MacAllister et al.

(10) Patent No.: US 11,311,553 B1
(45) Date of Patent: Apr. 26, 2022

(54) METHODS OF TREATING 4-REPEAT TAUOPATHIES

(71) Applicant: Woolsey Pharmaceuticals, Inc., New York, NY (US)

(72) Inventors: Thomas MacAllister, Arlington, VA (US); Sven Jacobson, New York, NY (US)

(73) Assignee: WOOLSEY PHARMACEUTICALS, INC., New York, NY (US)

(*) Notice: Subject to any disclaimer, the term of this patent is extended or adjusted under 35 U.S.C. 154(b) by 0 days.

(21) Appl. No.: 17/145,084

(22) Filed: Jan. 8, 2021

Related U.S. Application Data

(60) Provisional application No. 63/104,121, filed on Oct. 22, 2020.

(51) Int. Cl.
*A61K 31/551* (2006.01)

(52) U.S. Cl.
CPC .................... *A61K 31/551* (2013.01)

(58) Field of Classification Search
CPC .................................................. A61K 31/551
See application file for complete search history.

(56) References Cited

U.S. PATENT DOCUMENTS

| | | |
|---|---|---|
| 2010/0160297 A1 | 6/2010 | Nikolich et al. |
| 2018/0215758 A1 | 8/2018 | Accetta et al. |
| 2020/0101056 A1 | 4/2020 | Valera et al. |

FOREIGN PATENT DOCUMENTS

| | | |
|---|---|---|
| WO | 2005117896 A1 | 12/2005 |
| WO | 2008/019395 A2 | 2/2008 |
| WO | 2008/021210 A2 | 2/2008 |
| WO | 2009/151845 A1 | 12/2009 |
| WO | 2009155777 A1 | 12/2009 |
| WO | 2013135596 A1 | 9/2013 |
| WO | 2017/195224 A1 | 11/2017 |

OTHER PUBLICATIONS

Hamano et al. Neurobiology of Aging, May 2020, vol. 89, pp. 41-54 (Available Online Dec. 16, 2019) (Year: 2020).*
Koch et al. Pharmacology & Therapeutics, 2018, vol. 189, pp. 1-21 (Year: 2018).*
NCT00670202 (ClinicalTrials.gov, "Rho Kinase (ROCK) Inhibition in Carotid Atherosclerosis", NCT00670202, Last Update Posted Mar. 29, 2017, 7 pages) (Accessed from https://clinicaltrials.gov/ct2/show/record/NCT00670202?term=fasudil&draw=2&rank=9 on Mar. 16, 2021) (Year: 2017).*
Rosler et al. Progress in Neurobiology, 2019, vol. 180, Article 101644, pp. 1-31 (Year: 2019).*
Armstrong, Melissa et al., "Criteria for the diagnosis of corticobasal degeneration", Neurology, 2013, pp. 496-503, vol. 80, No. 5.
Barthelemy, Nicolas R. et al., "Blood plasma phosphorylated-tau isoforms track CNS change in Alzheimer's disease", Journal of Experimental Medicine, 2020, pp. 1-11, vol. 217, No. 11.
Bensimon, Gilbert et al., "Riluzole treatment, survival and diagnostic criteria in Parkinson plus disorders: the NNIPPS study", NNIPPS Study Group, Brain—A Journal of Neurology, Jan. 2009, pp. 156-171, vol. 132(Pt 1).
Boxer, Adam L. et al., "Davunetide in patients with progressive supranuclear palsy: a randomised, double-blind, placebo-controlled phase 2/3 trial", AL-108-231 Investigators, Lancet Neurol., Jul. 2014, pp. 676-685, vol. 13, No. 7.
Brendel, Matthias et al., "Assessment of 18F-PI-2620 as a Biomarker in Progressive Supranuclear Palsy", JAMA Neurology, Jul. 7, 2020, doi:10.1001/jamaneurol.2020.2526.
Chen, Meihui et al., "Fasudil and its analogs: A new powerful weapon in the long war against central nervous system disorders?" Expert Opin Investig. Drugs, 2013, pp. 537-550, vol. 22, No. 4.
Feng, Yangbo et al., "Rho Kinase (ROCK) Inhibitors and Their Therapeutic Potential", Journal of Medicinal Chemistry, 2016, pp. 2269-2300, vol. 59.
Gentry, Erik G. et al., "Rho Kinase Inhibition as a Therapeutic for Progressive Supranuclear Palsy and Corticobasal Degeneration", The Journal of Neuroscience, Jan. 27, 2016, pp. 1316-1323, vol. 36, No. 4.
Golbe, Lawrence et al., "A clinical rating scale for progressive supranuclear palsy", Brain, 2007, pp. 1552-1565, vol. 130.
Hamano, Tadanori et al., "Rho-kinase ROCK inhibitors reduce oligomeric tau protein", Neurobiology of Aging, 2020, pp. 1-14.
Hoglinger, Gunter U. et al., "Clinical diagnosis of progressive supranuclear palsy: The movement disorder society criteria", Movement Disorder Society-endorsed PSP Study Group, Jun. 2017, pp. 853-864, vol. 32, No. 6. total Tau, and pTau181, pTau202, pTau245, pTau377, and pTau409.
Jack, Jr., Clifford R. et al., "NIA-AA Reserach Framework: Toward a biological definition of Alzheimer's disease", Alzheimer's & Dementia, 2018, pp. 535-562, vol. 14.
Jacobs, Marc et al., "The structure of dimeric ROCK I reveals the mechanism for ligand selectivity", The Journal of Biological Chemistry, Jan. 6, 2006, pp. 260-268, vol. 281, No. 1.
Kumar, Manish et al., "Fasudil hydrochloride ameliorates memory deficits in rat model of streptozotocin-induced Alzheimer's disease: Involvement of PI3-kinase, eNOS and NFκB", Behavioural Brain Reserach, 2018, pp. 4-16, vol. 351.
Litvan, I. et al., "Clinical research criteria for the diagnosis of progressive supranuclear palsy (Steele-Richardson-Olszewski syndrome): Report of the NINDS-SPSP International Workshop", Neurology, 1996, pp. 1-9, vol. 47.

(Continued)

*Primary Examiner* — James D. Anderson
(74) *Attorney, Agent, or Firm* — McBee Moore & Vanik IP, LLC; Susan McBee; Chester Moore

(57) ABSTRACT

The present invention relates to the treatment patient with a 4-repeat (4R) tauopathy using a therapeutically effect amount of a rho kinase inhibitor. One preferred inhibitor is fasudil and preferred methods involve the daily oral administration of between 20 and 250 mg of fasudil. Preferred 4R tauopathies treatable according to the invention include progressive supranuclear palsy with Richardson syndrome (PSP-RS) and corticobasal syndrome with probable sporadic corticobasal degeneration.

18 Claims, No Drawings

(56) References Cited

OTHER PUBLICATIONS

Liu, Wenjun et al., "Absorption, tissue disposition, and excretion of fasudil hydrochloride, a RHO kinase inhibitor, in rats and dogs", Biopharm Drug Dispos, 2020, pp. 206-220, vol. 41.

Mao, Zhengsheng et al., "Aldehyde oxidase-dependent species difference in hepatic metabolism of fasudil to hydroxyfasudil", Xenobiotica, 2018, pp. 170-177, vol. 48, No. 2.

McKhann, Guy M. et al., "The diagnosis of dementia due to Alzheimer's disease: Recommendations from the National Institute on Aging-Alzheimer's Association workgroups on diagnostic guidelines for Alzheimer's disease", Alzheimers Dement., May 2011, pp. 263-269, vol. 7, No. 3.

Moretti, Davide Vito, "Available and future treatments for atypical parkinsonism. A systematic review", CNS Neurosci Ther., Feb. 2019, pp. 15-174,I vol. 25, No. 2.

Nakagawa, Osamu et al., "ROCK-1 and ROCK-II, two isoforms of Rho-associated coiled-coil forming protein serine/threonine kinase in mice," FEBS Letters, 1996, pp. 189-193, vol. 392.

Novak, Petr et al., "Ten Years of Tau-Targeted Immunotherapy: The Path Walked and the Roads Ahead", Frontiers in Neuroscience, Nov. 2, 2018, p. 798, vol. 12.

Panza, Francesco et al., "Development of disease-modifying drugs for frontotemporal dementia spectrum disorders", Nat Rev Neurol., 2020, pp. 213-228, vol. 16, No. 4.

Saijo, Eri et al., "4-Repeattau seeds and templating subtypes as brain and CSF biomarkers of frontotemporal lobar degeneration", Acta Neuropathol., Jan. 2020, pp. 63-77, vol. 139, No. 1.

Shibuya, M. et al., "Effect of fasudil HCI, a protein kinase inhibitor, on cerebral vasospasm", Acta Neurochir Suppl., 2001, pp. 201-204, vol. 77.

Stamelou, Maria et al., "Short-term effects of coenzyme Q10 in progressive supranuclear palsy: a randomized, placebo-controlled trial", Movement Disorders, May 15, 2008, pp. 942-949, vol. 23, No. 7.

Tolosa, Eduardo et al., "A phase 2 trial of the GSK-3 inhibitor tideglusib in progressive supranuclear palsy", Movement Disorders, Apr. 2014, pp. 470-478, vol. 29, No. 4.

Uehata, Masayoshi et al., "Calcium sensitization of smooth muscle mediated by a Rho-associated protein kinase in hypertension", Nature, Oct. 30, 1997, pp. 990-994, vol. 389, No. 6654.

Vandevrede, Lawren et al., "Open-Label Phase 1 Futility Studies of Salsalate and Young Plasma in Progressive Supranuclear Palsy", Movement Disorders Clinical Practice, Apr. 2020, pp. 440-447, vol. 7, No. 4.

Wetterling, Tilman et al., Comparison of Different Diagnostic Criteria for Vascular Dementia (ADDTC, DSM-IV, ICD-10, NINDS-AIREN), Stroke, Jan. 1, 1996, pp. 30-36, vol. 27.

Yamaguchi, Hiroto et al., "Molecular mechanism for the regulation of rho-kinase by dimerization and its inhibition by fasudil", Structure, Mar. 2006, pp. 589-600, vol. 14, No. 3.

Yanamandra, Kiran et al., "Anti-Tau Antibodies that Block Tau Aggregate Seeding In Vitro Markedly Decrease Pathology and Improve Cognition In Vivo", Neuron, 2013, pp. 402-414, vol. 80, No. 2.

Zhang, Wenjuan et al., "Novel tau filament fold in corticobasal degeneration", Nature, Apr. 2020, pp. 283-287, vol. 580, No. 7802.

Koch, Jan Christoph et al., "ROCK inhibition in models of neurodegeneration and its potential for clinical translation", Pharmacology & Therapeutics. 2018. 189: 1-21; Epub Apr. 23, 2018.

International Search Report of International Patent Application No. PCT/US21/12638 dated Mar. 26, 2021.

* cited by examiner

METHODS OF TREATING 4-REPEAT TAUOPATHIES

CROSS REFERENCE TO RELATED APPLICATIONS

This application claims priority to U.S. Provisional application 63/104,121, filed Oct. 22, 2020, the disclosure of which is incorporated herein by reference in its entirety.

BACKGROUND OF THE INVENTION

Proteinopathies are a group of conditions resulting from the improper folding or unfolding of a protein. They typically manifest as neurodegenerative disorders and are characterized by abnormal protein deposits or aggregates thought to result from conformational abnormalities that disrupt the normal placement of hydrophobic regions of the molecule into hydrophilic environments, causing the proteins to become insoluble and/or aggregate. In some cases, such as in prion diseases, the abnormal structures are thought to form nuclei for further protein deposition, initiating a kind of chain reaction of protein aggregation. The culprit proteins often are normal proteins with aggregates being formed after some post-translational modification, such as phosphorylation.

One example of this is the group of disorders known as tauopathies, which result in deposits of the microtubule-associated protein tau. Tau is a microtubule-associated protein that is predominantly expressed in neurons. In healthy subjects, tau is important in microtubule assembly, cellular transport, and DNA protection. Diseased tau instead creates oligomers and fibrils, destabilizes microtubules, damages the proteasome, causes neuronal and synaptic loss, and promotes neuroinflammation (Novak 2018). Its activity is regulated in part by alternative mRNA splicing of the MAPT (microtubule-associated protein tau) gene, which produces six different tau isoforms—three types containing three repeat regions (3R tau) and three types containing four repeat regions (4R tau) (Panza 2020). The binding of tau to microtubules is regulated by its phosphorylation-dephosphorylation equilibrium. Pathologic hyperphosphorylation of tau is one of the causes for tau to disengage from microtubules and aggregate. There is evidence that intercellular spread of tau aggregates can promote further aggregation in a prion-like manner. The amount of tau pathology correlates with progressive neuronal dysfunction, synaptic loss, and functional decline in humans and animal models (Yanamandra 2013).

Progressive supranuclear palsy (PSP), corticobasal degeneration (CBD), argyrophilic grain disease (AGD), and globular glial tauopathy (GGT) are considered to be progressive four repeat (4R) tauopathies, neuropathologically characterized by accumulation of phosphorylated 4R tau aggregates in neurons and certain glial cells.

At present, there is no effective therapy for any 4R tauopathy. In fact, every agent tested in the clinic thus far has failed to show an effect and most of these approaches involved directly antagonizing the pathologic effects of tau. While evidence suggested that mitochondrial dysfunction has a role in tauopathies, coenzyme Q10 (CoQ10) failed to provide benefit in PSP (Stamelou 2008). The inhibition of glycogen synthase kinase 3 (GSK-3) blocks tau phosphorylation, but lithium open-label trial in PSP was terminated due to poor tolerability (Moretti 2019) and tideglusib failed to show benefit in a phase 2 trial in PSP (Tolosa 2014). A phase 2-3 study of riluzole in PSP and multisystem atropy (MSA) failed to demonstrate effects (Bensimon 2009). Davunetide, a microtubule stabilizer was not shown not to be effective in PSP (Boxer 2014). Likewise, TPI 287 a taxane microtubule stabilizer also failed to show any effect in PSP (*Brain Support Network News release Dec.* 18, 2017, *Negative Results with TPI 287 in CBS and PSP*). Gosuranemab (BIIB092), a humanized monoclonal antibody that targets N-terminal tau, had no effect in a Phase 2 trial in PSP (*Biogen news release, Dec.* 13, 2019, *Biogen Reports Top-Line Results From Phase* 2 *Study In Progressive Supranuclear Palsy*). Another humanized anti-tau monoclonal antibody, ABBV-8E12, also failed to demonstrate an effect after enrolling 378 patients and was terminated for futility (*CurePSP Release Jul.* 29, 2019, *AbbVie Ends Tau Antibody Study*). Salsalate and young plasma have also failed in PSP studies (VandeVrede 2020). Thus, there is a wealth of evidence that pharmacological approaches and especially those aimed at disrupting tau pathology do not work and there is no expectation that any approach to disrupting tau pathology will work.

In addition to the usual problems of translating animal work to humans, fasudil, the prototypical rho kinase inhibitor, is known to have highly different metabolic profiles depending on species, including significant differences between the sexes in different animal species (Mao 2018; Liu 2020). Thus, because of the different metabolic profiles of different species and different sexes within each species, different animal models are actually testing different mixtures of active and inactive metabolites. Even in experiments using the same species, different mixtures are being tested between the two sexes. Without a complete understanding of the effects of these different mixtures and how they might relate to human metabolism (in males and females), there is no rational way to extrapolate from animal models to humans.

SUMMARY OF THE INVENTION

The invention contemplates the treatment of 4R tauopathies with rho kinase inhibitors. In a preferred embodiment, the rho kinase inhibitor is fasudil and it is administered orally in a daily dose of between 70 and 240 mg per day.

DETAILED DESCRIPTION OF THE INVENTION

The invention is based on the discovery that rho kinase inhibitors can be used to treat 4R tauopathies. Despite the failure of all approaches in the literature to treating any 4R tauopathy and especially those directed at tau pathology itself, the inventors have surprisingly discovered that with the appropriate treatment regimen in appropriate patients, rho kinase inhibitors may be successfully employed to treat these complicated conditions.

ROCK Inhibitors

The inventive methods contemplate the administration of a rho kinase (ROCK) inhibitor in the treatment of a disease or condition. Two mammalian ROCK homologs are known, ROCK1 (aka ROKβ, Rho-kinase β, or p160ROCK) and ROCK2 (aka ROKα) (Nakagawa 1996). In humans, the genes for both ROCK1 and ROCK2 are located on chromosome 18. The two ROCK isoforms share 64% identity in their primary amino acid sequence, whereas the homology in the kinase domain is even higher (92%) (Jacobs 2006; Yamaguchi 2006). Both ROCK isoforms are serine/threonine kinases and have a similar structure.

A large number of pharmacological ROCK inhibitors are known (Feng, LoGrasso, Defert, & Li, 2015). Isoquinoline derivatives are a preferred class of ROCK inhibitors. The isoquinoline derivative fasudil was the first small molecule ROCK inhibitor developed by Asahi Chemical Industry (Tokyo, Japan). The characteristic chemical structure of fasudil consists of an isoquinoline ring, connected via a sulphonyl group to a homopiperazine ring. Fasudil is a potent inhibitor of both ROCK isoforms. In vivo, fasudil is subjected to hepatic metabolism to its active metabolite hydroxyfasudil (aka, M3). Other examples of isoquinoline derived ROCK inhibitors include dimethylfasudil and ripasudil.

Other preferred ROCK inhibitors are based on based on 4-aminopyridine structures. These were first developed by Yoshitomi Pharmaceutical (Uehata et al., 1997) and are exemplified by Y-27632. Still other preferred ROCK inhibitors include indazole, pyrimidine, pyrrolopyridine, pyrazole, benzimidazole, benzothiazole, benzathiophene, benzamide, aminofurazane, quinazoline, and boron derivatives (Feng et al., 2015). Exemplary ROCK inhibitors are below:

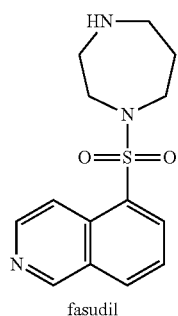

fasudil

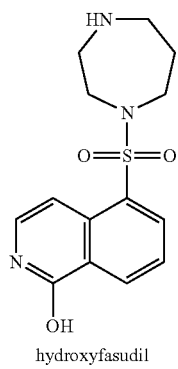

hydroxyfasudil

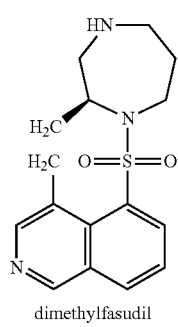

dimethylfasudil

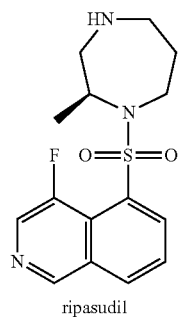

ripasudil

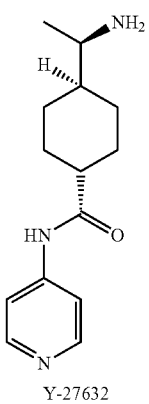

Y-27632

ROCK inhibitors according to the invention may have more selective activity for either ROCK1 or ROCK2 and will usually have varying levels of activity on PKA, PKG, PKC, and MLCK. Some ROCK inhibitors may be highly specific for ROCK1 or ROCK2 and have much lower activity against PKA, PKG, PKC, and MLCK.

A particularly preferred ROCK inhibitor is fasudil. Fasudil may exist as a free base or salt and may be in the form of a hydrate, such as a hemihydrate.

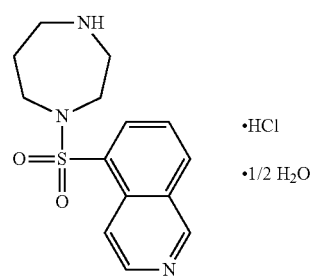 [SMILES: O=S(=O)(c1cccc2cnccc12)N1CCCNCC1 ; Cl]

Hexahydro-1-(5-isoquinolinesulfonyl)-1H-1,4-diazepine monohydrochloride hemihydrate Fasudil is a selective inhibitor of protein kinases, such as ROCK, PKC and MLCK and treatment results in a potent relaxation of vascular smooth muscle, resulting in enhanced blood flow (Shibuya 2001). A particularly important mediator of vasospasm, ROCK induces vasoconstriction by phosphorylating the myosin-binding subunit of myosin light chain (MLC) phosphatase, thus decreasing MLC phosphatase activity and enhancing vascular smooth muscle contraction. Moreover, there is evidence that fasudil increases endothelial nitric oxide synthase (eNOS) expression by stabilizing eNOS mRNA, which contributes to an increase in the level of the potent vasodilator nitric oxide (NO), thereby enhancing vasodilation (Chen 2013).

Fasudil has a short half-life of about 25 minutes, but it is substantially converted in vivo to its 1-hydroxy (M3) metabolite. M3 has similar effects to its fasudil parent molecule, with slightly enhanced activity and a half-life of about 8 hours (Shibuya 2001). Thus, M3 is likely responsible for the bulk of the in vivo pharmacological activity of the molecule. M3 exists as two tautomers, depicted below:

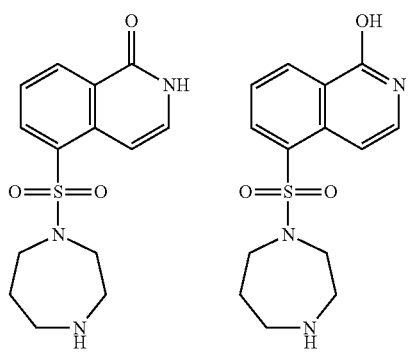

The ROCK inhibitors used in the invention, such as fasudil, include pharmaceutically acceptable salts and hydrates. Salts that may be formed via reaction with inorganic and organic acid. Those inorganic and organic acids are included as following: hydrochloric acid, hydrobromide acid, hydriodic acid, sulphuric acid, nitric acid, phosphoric acid, acetic acid, maleic acid, maleic acid, maleic acid, oxalic acid, oxalic acid, tartaric acid, malic acid, mandelic acid, trifluoroacetic acid, pantothenic acid, methane sulfonic acid, or para-toluenesulfonic acid.

Pharmaceutical Compositions

Pharmaceutical compositions of ROCK inhibitors usable in the are generally oral and may be in the form of tablets or capsules and may be immediate-release formulations or may be controlled- or extended-release formulations, which may contain pharmaceutically acceptable excipients, such as corn starch, mannitol, povidone, magnesium stearate, talc, cellulose, methylcellulose, carboxymethylcellulose and similar substances. A pharmaceutical composition comprising a ROCK inhibitor and/or a salt thereof may comprise one or more pharmaceutically acceptable excipients, which are known in the art. Formulations include oral films, orally disintegrating tablets, effervescent tablets and granules or beads that can be sprinkled on food or mixed with liquid as a slurry or poured directly into the mouth to be washed down.

Pharmaceutical compositions containing ROCK inhibitors, salts and hydrates thereof can be prepared by any method known in the art of pharmaceutics. In general, such preparatory methods include the steps of bringing a ROCK inhibitor or a pharmaceutically acceptable salt thereof into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. The composition used in accordance with the methods of the present invention may comprise between 0.001% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

In certain embodiments, the pharmaceutical composition used in the methods of the present invention may comprise a diluent. Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

In certain embodiments, the pharmaceutical composition used in the methods of the present invention may comprise a granulating and/or dispersing agent. Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM), sodium lauryl sulfate, quaternary ammonium compounds, and mixtures thereof.

In certain embodiments, the pharmaceutical composition used in the methods of the present invention may comprise a binding agent. Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan), alginates, polyethylene oxide, polyethylene glycol, inorganic calcium salts, silicic acid, polymethacrylates, waxes, water, alcohol, and/or mixtures thereof.

In certain embodiments, the pharmaceutical composition used in the methods of the present invention may comprise a preservative. Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

In certain embodiments, the pharmaceutical composition used in the methods of the present invention may comprise an antioxidant. Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

In certain embodiments, the pharmaceutical composition used in the methods of the present invention may comprise a chelating agent. Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

In certain embodiments, the pharmaceutical composition may comprise a buffering agent together with the ROCK inhibitor or the salt thereof. Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

In certain embodiments, the pharmaceutical composition used in the methods of the present invention may comprise a lubricating agent. Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

In other embodiments, the pharmaceutical composition of containing a ROCK inhibitor or salt thereof will be administered as a liquid dosage form. Liquid dosage forms for oral and parenteral administration include pharmaceutically acceptable emulsions, microemulsions, solutions, suspensions, syrups, and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Some compositions of the invention relate to extended- or controlled-release formulations. These may be, for example, diffusion-controlled products, dissolution-controlled products, erosion products, osmotic pump systems or ionic resin systems. Diffusion-controlled products comprise a water-insoluble polymer which controls the flow of water and the subsequent egress of dissolved drug from the dosage from. Dissolution-controlled products control the rate of dissolution of the drug by using a polymer that slowly solubilizes or by microencapsulation of the drug—using varying thicknesses to control release. Erosion products control release of drug by the erosion rate of a carrier matrix. Osmotic pump systems release a drug based on the constant inflow of water across a semi permeable membrane into a reservoir which contains an osmotic agent. Ion exchange resins can be used to bind drugs such that, when ingested, the release of drug is determined by the ionic environment within the gastrointestinal tract.

Methods of Treatment

The invention contemplates treating male or female human patients suspected of having diseases with an underlying 4R tauopathy. Preferred 4R tauopathies include PSP, CBD, AGD, GGT, which are neuropathologically characterized by accumulation of phosphorylated 4R tau aggregates in neurons and certain glial cells. Depending on the type and location of the specific pathology, 4R tauopathies may manifest as a number of different clinical syndromes, as described below. There is significant overlap between PSP and CBS (the clinical manifestation of CBD) and there is also significant similarity in the neuropathology, suggesting that they are highly related, if not manifestations of the same condition. A conclusive diagnosis of 4R tauopathies can only be made by examining the brain tissue, which can only be done by autopsy. Thus, patients treatable according to the invention will be considered to have "probable" or "possible" disease on this basis. For the purposes of the invention, these patients will be considered to have a 4R tauopathy, even though it has not been confirmed pathologically. In other words, as used herein, treatment of a patient with a 4-R tauopathy should be considered the treatment of a patient with probably or possible disease, as well as someone with the confirmed pathology should that become possible in the future without an autopsy, using, for example, imaging or biomarkers. Similarly, co-pathologies may also be present in patients treatable according to the invention. These include Alzheimer's disease-related pathology (including cerebral amyloid angiopathy), Lewy-related and transactive response DNA-binding protein 43 and other proteinopathies. Cerebrovascular disease, including small vessel disease is a common co-pathology.

Progressive Supranuclear Palsy

Current diagnostic criteria for PSP can be found in Höglinger 2017, which is incorporated by reference in its entirety. Probable PSP refers to a patient with confirmed diagnosis, for example, using the Höglinger criteria. Various clinical manifestations of probable PSP may be discerned, depending on the predominant clinical features. These include: PSP with Richardson's syndrome (PSP-RS); PSP with progressive gait freezing (PSP-PGF); PSP with predominant parkinsonism (PSP-P); PSP with predominant frontal presentation (PSP-F); PSP with predominant ocular motor dysfunction (PSP-OM); PSP with predominant speech/language disorder (PSP-SL); PSP with predominant CBS (PSP-CBS); PSP with predominant postural instability (PSP-PI). All of the foregoing manifestations are treatable according to the invention, but especially PAP-RS.

For a clinical diagnosis of PSP, it must be a sporadic occurrence; there should generally be no family history. Subjects must be Age 40 or older at onset of the first PSP-related symptom. There must be a gradual progression of PSP-related symptoms.

The clinical features of PSP can be divided into the following functional domains: ocular motor dysfunction, postural instability, akinesia and cognitive dysfunction. The mostly highly correlated ("Level 1") clinical features of PSP are vertical supranuclear gaze palsy, repeated unprovoked falls within 3 years, progressive gait freezing within 3 years, and speech/language disorder (nonfluent/agrammatic variant of primary progressive aphasia or progressive apraxia of speech). Also highly correlated with PSP ("Level 2" clinical features) are slow velocity of vertical saccades, a tendency to fall on the pull-test within 3 years, Parkinsonism, akinetic-rigid, predominantly axial, and levodopa resistant and frontal cognitive/behavioral presentation. Also significant, but somewhat less correlated ("Level 3" clinical features) are frequent macro square wave jerks or "eyelid opening apraxia"; more than two steps backward on the pull-test within 3 years, Parkinsonism, with tremor and/or asymmetric and/or levodopa responsive, and corticobasal syndrome. 1.1.1.1. Patients preferably treatable according to the invention will have at least one Level 1 or Level 2 clinical feature. Many patients will have a combination of clinical features drawn from the Level 1, Level 2 and Level 3 clinical features.

On the other hand, PSP is excluded if there is: a predominant, otherwise unexplained impairment of episodic memory, suggestive of Alzheimer's Disease (AD); a predominant, otherwise unexplained autonomic failure, e.g., orthostatic hypotension (orthostatic reduction in blood pressure after 3 minutes standing ≥30 mm Hg systolic or ≥15 mm Hg diastolic), suggestive of multiple system atrophy or Lewy body disease; a predominant, otherwise unexplained visual hallucinations or fluctuations in alertness, suggestive of dementia with Lewy bodies; a predominant, otherwise unexplained multisegmental upper and lower motor neuron signs, suggestive of motor neuron disease (pure upper motor neuron signs are not an exclusion criterion); a sudden onset or step-wise or rapid progression of symptoms, in conjunction with corresponding imaging or laboratory findings, suggestive of vascular etiology, autoimmune encephalitis, metabolic encephalopathies, or prion disease; a history of encephalitis; a prominent appendicular ataxia; or an identifiable cause of postural instability, e.g., primary sensory deficit, vestibular dysfunction, severe spasticity, or lower motor neuron syndrome.

PSP may also be excluded based on imaging findings: severe leukoencephalopathy, evidenced by cerebral imaging or a relevant structural abnormality, e.g., normal pressure or obstructive hydrocephalus; basal ganglia, diencephalic, mesencephalic, pontine or medullary infarctions, hemorrhages, hypoxic-ischemic lesions, tumors, or malformations.

In patients with sudden onset or step-wise progression, imaging should exclude stroke, cerebral autosomal dominant arteriopathy with subcortical infarcts and leukoencephalopathy (CADASIL) or severe cerebral amyloid angiopathy, evidenced by diffusion-weighted imaging (DWI), fluid attenuated inversion recovery, or T2-MRI. In patients with very rapid progression, cortical and subcortical hyperintensities on DWI-MRI suggestive of prion disease should be excluded.

In patients with PSP-CBS, primary AD pathology should be excluded using CSF biomarkers (both elevated total tau/phospho-tau protein and reduced β-amyloid 42) and/or β-amyloid PET imaging. In patients aged <45 years, the following should be ruled out: Wilson's disease (e.g., reduced serum ceruloplasmin, reduced total serum copper, increased copper in 24 hour urine, and Kayser-Fleischer corneal ring); Niemann-Pick disease, type C (e.g., plasma cholestan-3β,5a,6β-triol level, filipin test on skin fibroblasts); hypoparathyroidism; neuroacanthocytosis (e.g., Bassen-Kornzweig, Levine Critchley, McLeod disease); and neurosyphilis. In rapidly progressive patients, the following should be excluded: prion disease (e.g., elevated 14-3-3, neuron-specific enolase, very high total tau protein [>1,200 pg/mL], or positive real-time quaking-induced conversion in CSF); paraneoplastic encephalitis (e.g., anti-Ma1, Ma2 antibodies). In patients with suggestive features (i.e., gastrointestinal symptoms, arthralgias, fever, younger age, and atypical neurological features such as myorhythmia), exclude Whipple's disease (e.g., T. Whipple's disease DNA polymerase chain reaction in CSF).

In the event that there is evidence of a close family member with PSP, genetic testing should be done to rule out genetic disease. MAPT rare variants (mutations) are not exclusionary. MAPT H2 haplotype homozygosity is also not exclusionary, but it renders a PSP diagnosis unlikely. LRRK2 and Parkin rare variants have been observed in patients with autopsy confirmed PSP, but their causal relationship is unclear so far. Genetic polymorphism in the MAPT gene has been linked to increased risk for PSP; presence of a haplotype of an inverted sequence of polymorphisms in linkage disequilibrium (i.e. H1 haplotype) in MAPT has been linked to increased risk of PSPS in Caucasian populations.

The following are exclusionary because they may mimic aspects of PSP clinically, but differ neuropathologically: non-MAPT associated frontotemporal dementia (e.g., C9orf72, GRN, FUS, TARDBP, VCP, CHMP2B); PD (e.g., SYNJ1, GBA); AD (APP, PSEN1, PSEN2); Niemann-Pick disease, type C (NPC1, NPC2); Kufor-Rakeb syndrome (ATP13A2); Perry syndrome (DCTN1); mitochondrial diseases (POLG, mitochondrial rare variants); dentatorubral pallidoluysian atrophy (ATN1); prion-related diseases (PRNP); Huntington's disease (HTT); and spinocerebellar ataxia (ATXN1, 2, 3, 7, 17).

Corticobasal Syndrome

Current diagnostic criteria for CBS can be found in Armstrong 2013, which is incorporated by reference in its entirety. The following table describes the various types of treatable corticobasal degeneration patients treatable according to the invention. Preferred embodiments contemplate treating patients with probable corticobasal syndrome and/or probable corticobasal degeneration.

| CBD Clinical Syndromes | |
|---|---|
| Syndrome | Features |
| Probable corticobasal syndrome | Asymmetric presentation of 2 of: a) limb rigidity or akinesia, b) limb dystonia, c) limb myoclonus plus 2 of: d) orobuccal or limb apraxia, e) cortical sensory deficit, f) alien limb phenomena (more than simple levitation) |
| Possible corticobasal syndrome | May be symmetric: 1 of: a) limb rigidity or akinesia, b) limb dystonia, c) limb myoclonus plus 1 of: d) orobuccal or limb apraxia, e) cortical sensory deficit, f) alien limb phenomena (more than simple levitation) |
| Frontal behavioral-spatial syndrome (FBS) | Two of: a) executive dysfunction, b) behavioral or personality changes, c) visuospatial deficits |
| Nonfluent/agrammatic variant of primary progressive aphasia (NAV) | Effortful, agrammatic speech plus at least one of: a) impaired grammar/sentence comprehension with relatively preserved single word comprehension, or b) groping, distorted speech production (apraxia of speech) |
| Progressive supranuclear palsy syndrome (PSPS) | Three of: a) axial or symmetric limb rigidity or akinesia, b) postural instability or falls, c) urinary incontinence, d) behavioral changes, e) supranuclear vertical gaze palsy or decreased velocity of vertical saccades |

| Diagnostic criteria for corticobasal degeneration | | |
|---|---|---|
| | Clinical research criteria for probable sporadic CBD | Clinical criteria for possible CBD |
| Presentation | Insidious onset and gradual progression | Insidious onset and gradual progression |
| Minimum duration of symptoms, y | 1 | 1 |
| Age at onset, y | 50 | No minimum |
| Family history (2 or more relatives) | Exclusion | Permitted |
| Permitted phenotypes (see table 4 for criteria) | 1) Probable CBS or 2) FBS or NAV plus at least one CBS feature (a-f) | 1) Possible CBS or 2) FBS or NAV or 3) PSPS plus at least one CBS feature b-f |
| Genetic mutation affecting tau (e.g., MAPT) | Exclusion | Permitted |

The same exclusions, especially for AD should be applied in the same manner with CBS as with PSP.

Argyrophilic Grain Disease

AGD presents with no unique clinical features. Most significantly, AGD manifest as AD and so for the purposes of the present invention, AGD can be considered to be clinically the same as AD, but with evidence that the patient lacks amyloid pathology. Amyloid pathology may be discounted by examining CSF levels of β-amyloid 42 and/or using β-amyloid PET imaging. It has been reported that AGD lacks acetylated tau in inclusions compared to other 4R tauopathies.

Globular Glial Tauopathy

Like AGD, GGT has no defining clinical syndrome, presenting with a combination of frontotemporal dementia, motor neuron disease and/or extrapyramidal features. Identification of GGT patients will rely on eliminating other pathologies using imaging, biomarkers and differential diagnosis.

Diagnosis of 4R tauopathies aided using imaging and measuring biomarkers in cerebrospinal fluid (CSF). The most widely used CSF biomarkers for AD (to eliminate this pathology) measure certain proteins: beta-amyloid 42 (the major component of amyloid plaques in the brain), tau, and phospho-tau (major components of tau tangles in the brain). In AD, beta-amyloid 42 levels in CSF are low, compared with levels in people without Alzheimer's or other causes of dementia (Jack 2018).

Imaging is as useful tool in diagnosing neurodegenerative conditions, including 4R tauopathies, in particular computerized tomography (CT), magnetic resonance imaging (MRI) and positron emission spectroscopy (PET). Neural degeneration results in brain atrophy and this can be detected and quantified. Automated tools are increasingly available that can perform these functions.

Fluorodeoxyglucose (FDG) PET scans measure glucose use in the brain. Glucose, a type of sugar, is the primary source of energy for cells. Studies show that people with neurodegeneration often have abnormal patterns of decreased glucose use in specific areas of the brain. An FDG PET scan can show a pattern that may support a diagnosis. 4R-tauopathies are associated with frontal, caudate, and thalamic hypometabolism on FDG-PET (Zalewski 2014).

Amyloid PET scans measure abnormal deposits of a protein called beta-amyloid. Higher levels of beta-amyloid are consistent with the presence of amyloid plaques, a hallmark of AD. Several tracers may be used for amyloid PET scans, including florbetapir, flutemetamol, florbetaben, Pittsburgh compound B and NAV4694.

Tau PET scans detect abnormal accumulation of a protein, tau, which forms tangles in nerve cells in 4R tauopathies. Several tau tracers, such as AV-1451 (Flortaucipir), PI-2620, and MK-6240, are being studied in clinical trials and other research settings. $^{18}$F-PI-2620 recently was shown to differentiate PSP from other tauopathies (Brendel 2020). One exemplary tracer is [18F]FDDNP, which is retained in the brain in individuals with progressive supranuclear palsy and corticobasal degeneration. Other tau tracers include [18F]-T807, [18F]T808, [18F]THK5117(5317), [18F]THK5351, [11C]PBB3, [18F]PM-PBB3, [18F]RO69558948, and [18F]GTP1. Recently, it was discovered that tau from patients with a 4R tauopathy was in a different folded form than that from AD, CTE or Pick disease patients, suggesting that tracers specific to this fold could be diagnostic. (Zhang 2020). In addition, the folded tau was associated with dense, non-tau molecules that were determined to be composed of acetyl, and ubiquitin. In addition, other residues of the tau from the 4R diseases were phosphorylated as expected, but also acetylated and ubiquitinated in an opposite pattern as found in tau from AD.

Recently, scientists adapted a test from one used to differentiate AD from CTE in CSF to specifically detects among the 4R tauopathies in CSF. The test, 4R RT-QuIC which stands for 4-repeat tau protein amplified in a real-time, quaking-induced conversion process, detects conformational variations in 4R tauopathies that are different from other tauopathies. (Saijo 2020).

In accordance with the treatment methods of the present invention, administering a therapeutically effective amount of a ROCK inhibitor or a pharmaceutically acceptable salt thereof one or more times a day. The lowest therapeutically effective amount of fasudil, for example, is 70 mg per day, generally administered in 2 to 3 equal portions to obtain the full daily dose. The highest therapeutically effective dose may be determined empirically as the highest dose that remains effective in alleviating one or more related signs or symptoms, but does not induce an unacceptable level or adverse events. Fasudil, for example, generally will not be administered in a daily dose exceeding 180 mg, but in some cases 240 mg may be appropriate. One preferred dosing regimen involves the treatment with 25, 30, 40 or 60 mg of Fasudil hydrochloride hemihydrate three times per day using an immediate-release formulation, for a total daily dose of 75-180 mg. Preferred dosing exceeds a daily dose of 70 mg, with most preferred ranges for daily dosing being 70 mg to 140 mg administered in three equal amounts during the day. Other preferred daily doses will range from 90 mg to 180 mg per day or 80 mg to 150 mg orally per day. A further dosing regimen involves the treatment with, 35 to 90 mg of Fasudil hydrochloride hemihydrate only two times per day using an immediate-release formulation, for a total daily dose of 70-180 mg. Generally, an oral daily dose of 70-75 mg will the minimum required to see a treatment effect. At more than 180 mg per day given orally, kidney function begins to be affected and higher dosing in most patients will not be warranted. Above 240 mg per day, kidney effects of the drug are generally unacceptable. Based on ROCK inhibitory activity, one skilled in the art can readily extrapolate the provided dosing ranges for fasudil to other ROCK inhibitors.

The treatment methods of the present invention, while contemplating various routes of administration, are particularly suited to oral administration. Thus, it will be understood that an effective amount of a ROCK inhibitor or a pharmaceutically acceptable salt thereof preferably is administered orally one or more times orally per day and an effective amount may range from the lowest therapeutically effective amount of fasudil, which is 70 mg per day. Generally, it will be administered orally in 2 to 3 equal portions to obtain the full daily dose. The daily oral dose of fasudil, for example, generally will not exceed 180 mg. One preferred dosing regimen involves the treatment with 25, 30, 40 or 60 mg of Fasudil hydrochloride hemihydrate three times per day orally using an immediate-release formulation, for a total daily dose of 75-180 mg. Preferred dosing exceeds a oral daily dose of 70 mg, with most preferred ranges for daily dosing being 70 mg to 140 mg administered in three equal amounts orally during the day. Other preferred daily doses will range from 90 mg to 180 mg per day or 80 mg to 150 mg orally per day. A further dosing regimen involves the treatment with, 35 to 90 mg of Fasudil hydrochloride hemihydrate only two times per day using an immediate-release oral formulation, for a total daily dose of 70-180 mg. Generally, an oral daily dose of 70-75 mg will the minimum required to see a treatment effect. At more than 180 mg per day given orally, kidney function begins to be affected and higher dosing in most patients will not be warranted. Above 240 mg per day orally, kidney effects of the drug are generally unacceptable. Based on ROCK inhibitory activity, one skilled in the art can readily extrapolate the provided dosing ranges for fasudil to other ROCK inhibitors.

Certain patient sub-populations, such as renally impaired patients and/or older patients (e.g., 65 or older) may need lower doses or extended release formulations instead of immediate release formulations. Fasudil hydrochloride hemihydrate may have higher steady-state concentrations when given at usual doses to patients with renal disease and lower doses to lower the Cmax or delay the time to Cmax (increase the Tmax) may be required.

Renal dysfunction occurs with age and as the result of numerous disorders, including liver cirrhosis, chronic kidney disease, acute kidney injury (for example, due to administering a contrast agent), diabetes (Type 1 or Type 2), autoimmune diseases (such as lupus and IgA nephropathy), genetic diseases (such as polycystic kidney disease), nephrotic syndrome, urinary tract problems (from conditions such as enlarged prostate, kidney stones and some cancers), heart attack, illegal drug use and drug abuse, ischemic kidney conditions, urinary tract problems, high blood pressure, glomerulonephritis, interstitial nephritis, vesicoureteral, pyelonephritis, sepsis. Kidney dysfunction may occur in other diseases and syndromes, including non-kidney-related diseases that may occur along with kidney dysfunction, for example pulmonary artery hypertension, heart failure, and cardiomyopathies, among others.

Kidney function is most often assessed using serum (and/or urine) creatinine. Creatinine is a breakdown product of creatine phosphate in muscle cells and it is produced at a constant rate. It is excreted by the kidneys unchanged, principally through glomerular filtration. Accordingly, elevated serum creatinine is a marker for kidney dysfunction and it is used to estimate glomerular filtration rate.

Normal levels of creatinine in the blood are approximately 0.6 to 1.2 mg/dL in adult males and 0.5 to 1.1 mg/dL in adult females. When creatinine levels exceed these figures, the subject has renal dysfunction, and is, therefore, treatable according to the invention. Mild renal impairment/dysfunction occurs in the range of 1.2 mg/dL to 1.5 mg/dL. Moderate renal impairment/dysfunction is considered to occur at creatinine levels exceeding 1.5 mg/dL. Severe renal impairment, which includes what is considered to be renal failure, is defined as a serum creatinine level of ≥2.0 mg/dL or the use of renal replacement therapy (such as dialysis). Treating subjects with mild, moderate and severe renal impairment is specifically contemplated.

As indicated, creatinine levels are considered to be a surrogate for glomerular filtration rate (GFR) and serum creatinine levels alone may be used to estimate glomerular filtration rate using the Cockroft-Gault equation.

According to the National Kidney Foundation, the following GFRs indicate the varying levels of renal function:

| GFR (ml/min/1.73 m$^2$) | Renal Function |
| --- | --- |
| ≥90 | Normal or high |
| 60-89 | Mildly decreased |
| 45-59 | Mildly to moderately decreased |
| 30-44 | Moderately to severely decreased |
| 15-29 | Severely decreased |
| <15 | Kidney failure |

In general, creatinine clearance (estimated glomerular filtration rate) may be derived directly from serum creatinine using the Cockroft-Gault equation:

creatinine clearance=(((140−age in years)×(wt in kg))×1.23)/(serum creatinine in mol/L)

For women the result of the calculation is multiplied by 0.85.

Empirically measured creatinine clearance may also be used directly as an estimate of glomerular filtration rate by looking at serum creatinine and urine creatinine levels. Specifically, urine is collected over 24 hours and the following equation is applied to ascertain creatinine clearance:

Creatinine Clearance (mL/min)=Urine Creatinine Concentration (mg/mL)*24 hour urine volume (mL)/Plasma Creatinine Concentration (mg/mL) *24 hour*60 minutes In one embodiment, dose of fasudil for mild to moderate renal impairment is reduced to 50-80 mg per day. In another embodiment, the dose of fasudil is not reduced but is administered one time per day in an extended release dosage form.

In another embodiment, the dose is not reduced for mild to moderate renal impairment.

In one embodiment, the dose of fasudil is reduced to 30-45 for severe renal impairment. In another embodiment, the dose of fasudil is not reduced but is instead administered one time per day in an extended release dosage form.

In a further embodiment, the dose is reduced where serum creatinine (SCr)>2 and/or an increase in SCr>1.5× from baseline, and/or a decrease in eGFR>25% from baseline.

Patient size is an important factor to consider when using creatinine-based estimates of renal function. The units of drug clearance are volume/time (mL/min), whereas the units of estimated GFR for chronic renal disease are volume/time/standard size (mL/min/1.73 m$^2$). Generally, doses may be adjusted down (e.g., 40-50 mg per day) for smaller patients and up for larger (e.g., 120 mg per day) for obese patients. A smaller male would be about 160 pounds or less. A smaller female patient would weigh about 130 pounds or less. Patients having a Body Mass Index of 30 and higher is considered obese.

In addition, older patients may need a lower dose at initiation, with a gradual increase to the recommended dose after days or weeks. In another embodiment, older patients may need lower doses for the duration of treatment. The aged population includes the "young old" who are 65-74, the "old old" who are 75-84 and the "frail elderly" who are 85 and older. For example, a starting dose of 30 mg per day for two weeks, followed by 60 mg per day for 4 weeks, then by 90 mg per day. Titration may even be warranted up to about 120 mg per day.

Another embodiment involves the treatment with 60-120 mg of fasudil hydrochloride hemihydrate once per day in an extended release dosage form. Treatment with an extended release total daily dose of 90 mg fasudil hydrochloride hemihydrate once per day is preferred. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Methods of administering compositions according to the invention would generally be continued for at least one day. Some preferred methods treat for up to 30 days or up to 60 days or even up to 90 days or even more. Treatment for more than 60 days is preferred and treatment for at least 6 months is particularly preferred. The precise duration of treatment will depend on the patient's condition and response to treatment. Most preferred methods contemplate that treatment begins after the onset or appearance of symptoms.

Another embodiment involves the treatment with 60-120 mg of Fasudil hydrochloride hemihydrate once per day in an extended release dosage form. Treatment with an extended release total daily dose of 90 mg Fasudil hydrochloride hemihydrate is preferred.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Methods of administering compositions according to the invention would generally be continued for at least one day. Some preferred methods treat for up to 30 days or up to 60 days or even up to 90 days or even more. Treatment for more than 60 days is preferred and treatment for at least 6 months is particularly preferred. The precise duration of treatment will depend on the patient's condition and response to treatment.

Patients treatable according to the invention are preferably mostly cognitively intact with mini a mental state exam (MMSE) score of at least 20.

The progressive supranuclear palsy rating scale (PSPRS) is a useful tool in evaluating the severity of and monitoring the progression of PSP (Golbe 2007), but it may also be used with CBS patients. It assesses 6 domains (history, mentation, bulbar, oculomotor, limb motor, gait and midline) using 28 assessments, each of which have a severity rating ranging from 0 (normal) to 2-4, depending on the specific assessment for total scores ranging from 0 to 100. A patient treated according to the invention will have a PSPRS score of at least before beginning therapy and preferable a PSPRS score of at least 20. The mean rate of progression of PSP patient is 9.7 points per year and the methods of treatment can reduce this rate of progression by 10%, 20%, 30%, 40%, 50% or more, potentially delaying the onset of complete disability and prolonging quality of life. Improvements may be observed on the entire scale or on one or more of the domains.

The corticobasal degeneration functional scale (CBD-FS) may also be employed to evaluate CBS patients. It consists of three domains: motor experiences of daily living, language/cognitive/behavioral, and other non-motor activities of daily living. Motor experiences assesses: speaking; saliva & drooling; eating tasks; chewing and swallowing; dressing; hygiene; handwriting or typing; doing hobbies and leisure activities; turning in bed; getting into or out of bed, a car or a deep chair; walking and balance once standing; and spontaneously voluntary movements. Language/cognitive/behavioral assessments: reading comprehension; thinking clearly; memory; managing finances; performing complex or multiple tasks; acting appropriately around others; doing things repetitively over and over; diet and food preferences; mood; anxiety; motivation; caring about others; and agitation. Non-motor activities of daily living assessments: sleeping at night; staying awake during the day; physical or mental fatigue; urinary control; visual problems; and way-finding and navigation.

The pathological transformation of tau is related to phosphorylation, which not only causes tau to disassociate from microtubules, but it makes tau more likely to aggregate and contribute to disease progression. The inventive methods result in the reduction of tau phosphorylation in specific regions at specific amino acid residues associated with pathological tau. Typically, these amino acids are located in the proline-rich region, adjacent to the microtubule binding domains, or in the far C-terminal region. Phosphorylated residues that are affected by the inventive methods and are, thus, indicative of a treatment effect, include one or more of the following:

| Amino Acid | Position |
| --- | --- |
| Tyrosine | 18, 197, 310, 394 |
| Serine | 46,68, 113, 131, 181, 185, 191, 198, 199, 202, 214, 235, 237, 238, 258, 262, 285, 289, 293, 305, 324, 356, 396, 400. 404, 412, 413, 416, 422, 433, 435 |
| Threonine | 52, 69, 71, 123, 149, 153, 175, 181, 184, 205, 212, 217, 231, 403, 427 |

Other modifications include acetylation of tau at lysine 280 in the second microtubule binding domain of 4R-tau. In CBD, ubiquitinated K353 and acetylated K343 were found in twisted fibrils. The reverse, acetylated K353 and ubiquitinated K343, modified straight tau filaments.

In assessing this effect of the inventive methods on tau pathology, the most sensitive method would examine the CSF using mass-spectrometry (Barthelemy 2020), but antibodies that detect certain phosphorylated residues may also be employed in this regard:

| Antibody | Phosphorylation Site Detected |
| --- | --- |
| AT270 | T181 |
| AT8 | S202/T205 |
| AT100 | T212/S214 |
| AT180 | T231 |
| TG3 | S235/T231 |
| PHF-1/AD2 | S396/S204 |
| AP422 | S422 |

Other outcomes contemplated by the instant invention include improvement in Levels 1-3 clinical features for PSP including vertical supranuclear gaze palsy, repeated unprovoked falls within 3 years, progressive gait freezing within 3 years, and speech/language disorder (nonfluent/agrammatic variant of primary progressive aphasia or progressive apraxia of speech, slow velocity of vertical saccades, a tendency to fall on the pull-test within 3 years, Parkinsonism, akinetic-rigid, predominantly axial, frontal cognitive/behavioral presentation, frequent macro square wave jerks or "eyelid opening apraxia"; more than two steps backward on the pull-test within 3 years, and corticobasal syndrome. The invention also contemplates delaying the progression of disease a 4R tauopathy.

The methods of the invention also contemplate administering ROCK inhibitors with other compounds used to treat 4R tauopathies and other symptoms of 4R tauopathies. They may be administered in combination, a single dosage form, in a common dosing regimen or administered to the same patient at different times of the day using different dosing regimens.

In some embodiments, the patients are administered fasudil in combination with other neurotropic actives, including but not limited to cholinesterase inhibitors and NMDA receptor antagonists. In one embodiment, the cholinesterase inhibitor is selected from the group consisting of donepezil, rivastigmine, and galantamine. Exemplary doses of the cholinesterase inhibitors include 3-25 mg per day, more preferably 6-12 mg per day. In another embodiment, the NMDA receptor antagonist is memantine. In a specific embodiment, memantine is administered at a dose of 5-28 mg per day, preferably 15-20 mg per day. In a further embodiment, the co-administered active is a combination of donepezil and memantine at a dose of 28 mg memantine and 10 mg donepezil. It is further contemplated that a treatment regimen may also include anti-tau antibodies in combined regimen that may be administered together with or separately from rho kinase inhibitors.

In a specific embodiment, the combination of fasudil with cholinesterase inhibitors is administered to patients with a 4R tauopathy.

Dextromethorphan hydrobromide is another an uncompetitive NMDA receptor antagonist that also has activity as a sigma-1 receptor agonist. Marketed in combination quinidine sulfate (a CYP450 2D6 inhibitor), the product Nudexta is indicated for the treatment of pseudobulbar affect, which may also occur in 4R tauopathies.

In another embodiment, the patient is administered fasudil in combination with levodopa or a dopamine agonist (with or without a monoamine oxidase inhibitor or other metabolic modifier), including but not limited to pramiprexole, ropinirole, apomorphine, and rotigotine. In a specific embodiment, the levodopa is administered in a dose of from about 30 to 2500 mg per day. In a further specific embodiment, the dopamine agonist is administered in a dose of from 0.25 to 10 mg per day. In another embodiment, fasudil is administered in combination with amantadine. In a specific embodiment, amantadine is administered in a dose of about 100-400 mg per day.

In yet another embodiment the patient is administered fasudil in combination with riluzole or edavarone at about 50 to 100 mg day.

In a further embodiment, the patient is administered fasudil in combination with tau aggregation inhibitors including ACI-3024, and immunotherapy, or vaccines that mimic the phospho-epitope of tau.

In a further embodiment, the patient treated with fasudil is not also being treated with active agents including mood stabilizers, benzodiazepines, antipsychotics, anti-agitation drugs, or sleep aids. In a specific embodiment, the patient treated with fasudil is not being treated with risperidone, aripriprazole, quetiapine, carbamazepine, gabapentin, prazosin, trazodone or lorazepam.

In a further embodiment the patient treated with fasudil is being treated for depression. In a specific embodiment, the patient is treated with an anti-depressant such as citalopram or escitalopram.

Examples

Ten subjects 50-85 years old, meeting the National Institute of Neurological Disorders and Stroke-Society for Progressive Supranuclear Palsy (NINDS-SPSP) probable or possible PSP criteria, (Litvan 1996) as modified from the AL-108-231 trial (Boxer 2014) are enrolled. MRI at screening is consistent with PSP (≤4 microhemorrhages and no large strokes or severe white matter disease). They have Mini-Mental State Examination (MMSE) score 14-30 and have stable medications for 2 months prior to screening, including FDA approved Alzheimer's disease (AD) medications and Parkinson's disease medications. Subjects are excluded if they meet the National Institute on Aging-Alzheimer's Association Workgroups criteria for probable AD (McKhann 2011), if they have any medical condition other than PSP that could account for cognitive deficits (e.g., active seizure disorder, stroke, vascular dementia) or if they have a prominent and sustained response to levodopa therapy (suggestive of Parkinson's disease). Patients are also excluded if they have a history of significant cardiovascular, hematologic, renal, or hepatic disease (or laboratory evidence thereof), a history of major psychiatric illness or untreated depression, serum creatinine ≥1.5 mg/dL, blood pressure <90/60, or evidence of orthostatic hypotension.

All assessments, including MRI and lumbar puncture are performed at baseline, six months and one year. Patients are treated with fasudil at a dose of 180 mg/day (60 mg tid). Assessments at six months and one year as compared to baseline include:
  Changes in motor function, cognition, activities of daily living, and behavior as measured by the Progressive Supranuclear Palsy Rating Scale (PSPRS)
  Changes in motor function, cognition, activities of daily living, and behavior as measured by Schwab and England Activities of Daily Living scale (SEADL)
  Changes in Clinical Global Severity Scale (CGI-S)
  Changes in Clinical Dementia Rating Scale sum of boxes (CDR-SB)
  Changes in Repeatable Battery for the Assessment of Neuropsychological Status (RBANS)
  Changes in Geriatric Depression Scale (GDS)
  Changes in concentration of cerebrospinal fluid (CSF) biomarkers including neurofilament light chain (NfL) concentrations, Amyloid Beta (AB), total Tau, and phosphorylated tau species, including pTau181, pTau 202, pTau245, pTau377, and pTau409.
  Changes in brain volume [T1-weighted volumetric magnetic resonance imaging (vMRI)], brain network functional and structural connectivity and perfusion [resting state functional magnetic resonance imaging (rsfMRI), diffusion tensor imaging (DTI), and arterial spin labeling (ASL) perfusion magnetic resonance imaging (MRI)]
  Changes in saccade eye movements, specifically changes in saccade latency, velocity, and amplitude [infrared oculometry]
  Changes in sleep and activity levels using actigraphic measures Comparisons are also made to historical controls. Approximately 50% of patients respond to treatment as evidenced by slowed deterioration on one or more rating scales. In particular, the PSP-RS shows a 5-point or less increase over a year, whereas the average is closer to 10. Brain atrophy likewise progresses more slowly in treated subjects. Finally, treated subjects show reduced overall tau and Nfl, as well as a reduced ratio of phosphorylated tua species to total tau as compared both their baseline levels and as compared to historical controls. Oculomotor and sleep parameters also improve.

LIST OF REFERENCES

Armstrong M J, Litvan I, Lang A E, Bak T H, Bhatia K P, Borroni B, et al. Criteria for the diagnosis of corticobasal degeneration. Neurology. 2013; 80(5):496-503.

Barthelemy R, Horie K, Sato, C, Bateman R, Blood plasma phosphorylated-tau isoforms track CNS change in Alzheimer's disease. J. Exp. Med. 2020; 217(11): 1-11.

Bensimon G, Ludolph A, Agid Y, Vidailhet M, Payan C, Leigh P N; NNIPPS Study Group. Riluzole treatment, survival and diagnostic criteria in Parkinson plus disorders: the NNIPPS study. Brain. 2009 January; 132(Pt 1):156-71.

Boxer A L, Lang A E, Grossman M, Knopman D S, Miller B L, Schneider L S, Doody R S, Lees A, Golbe L I, Williams D R, Corvol J C, Ludolph A, Burn D, Lorenzl S, Litvan I, Roberson E D, Höglinger G U, Koestler M, Jack C R Jr, Van Deerlin V, Randolph C, Lobach I V, Heuer H W, Gozes I, Parker L, Whitaker S, Hirman J, Stewart A J, Gold M, Morimoto B H; A L-108-231 Investigators. Davunetide in patients with progressive supranuclear palsy: a randomised, double-blind, placebo-controlled phase 2/3 trial. Lancet Neurol. 2014 Jul.; 13(7):676-85.

Brendel M, Barthel H, van Eimeren T, Assessment of 18F-PI-2620 as a Biomarker in Progressive Supranuclear Palsy. JAMA Neurol. Jul. 7, 2020 doi:10.1001/jamaneurol.2020.2526.

Chen M, Liu A, Ouyang Y, Huang Y, Chao X, Pi R. 2013. Fasudil and its analogs: a new powerful weapon in the long war against central nervous system disorders? Expert Opin Investig Drugs. 22:537-50.

Feng Y, LoGrasso P V, Defert O, Li R. Rho Kinase (ROCK) Inhibitors and Their Therapeutic Potential. J Med Chem. 2015 Mar. 24; 59(6):2269-300.

Golbe L I and Strickland P A, A clinical rating scale for progressive supranuclear palsy. Brain (2007), 130, 1552-1565.Höglinger G U, Respondek G, Stamelou M, Kurz C, Josephs K A, Lang A E, Mollenhauer B, Müller U, Nilsson C, Whitwell J L, Arzberger T, Englund E, Gelpi E, Giese A, Irwin D J, Meissner W G, Pantelyat A, Rajput A, van Swieten J C, Troakes C, Antonini A, Bhatia K P, Bordelon Y, Compta Y, Corvol J C, Colosimo C, Dickson D W, Dodel R, Ferguson L, Grossman M, Kassubek J, Krismer F, Levin J, Lorenzl S, Morris H R, Nestor P, Oertel W H, Poewe W, Rabinovici G, Rowe J B, Schellenberg G D, Seppi K, van Eimeren T, Wenning G K, Boxer A L, Golbe L I, Litvan I; Movement Disorder Society-endorsed PSP Study Group. Clinical diagnosis of progressive supranuclear palsy: The movement disorder society criteria. Mov Disord. 2017 June; 32(6):853-864. total Tau, and pTau181, pTau 202, pTau245, pTau377, and pTau409

Jacobs M, Hayakawa K, Swenson L, Bellon S, Fleming M, Taslimi P, Doran J. The structure of dimeric ROCK I reveals the mechanism for ligand selectivity. J Biol Chem. 2006 Jan. 6; 281(1):260-8.

Litvan I, Agid Y, Calne D, Campbell G, Dubois B, Duvoisin R C, Goetz C G, Golbe L I, Grafman J, Growdon J H, Hallett M, Jankovic J, Quinn N P, Tolosa E, Zee D S. Clinical research criteria for the diagnosis of progressive supranuclear palsy (Steele-Richardson-Olszewski syndrome): Report of the NINDS-SPSP International Workshop. Neurology 1996; 47:1-9

Liu W, Gao J, Yi X, Li Y, Zeng Y. Absorption, tissue disposition, and excretion of fasudil hydrochloride, a RHO kinase inhibitor, in rats and dogs. Biopharm Drug Dispos. 2020; 41:206-220. Mao Z, Wu Y, Li Q, Wang X, Liu Y & Di X. 2018. Aldehyde oxidase-dependent species difference in hepatic metabolism of fasudil to hydroxyfasudil. Xenobiotica, 48:2, 170-177.

Jack C R Jr, Bennett D A, Blennow K, Carrillo M C, Dunn B, Haeberlein S B, Holtzman D M, Jagust W, Jessen F, Karlawish J, Liu E, Molinuevo J L, Montine T, Phelps C, Rankin K P, Rowe C C, Scheltens P, Siemers E, Snyder H M, Sperling R; Contributors. NIA-AA Research Framework: Toward a biological definition of Alzheimer's disease. Alzheimers Dement. 2018 Apr.; 14(4):535-562.

McKhann G M, Knopman D S, Chertkow H, Hyman B T, Jack C R Jr, Kawas C H, Klunk W E, Koroshetz W J, Manly J J, Mayeux R, Mohs R C, Morris J C, Rossor M N, Scheltens P, Carrillo M C, Thies B, Weintraub S, Phelps C H. The diagnosis of dementia due to Alzheimer's disease: recommendations from the National Institute on Aging-Alzheimer's Association workgroups on diagnostic guidelines for Alzheimer's disease. Alzheimers Dement. 2011 May; 7(3):263-9.

Moretti D V. Available and future treatments for atypical parkinsonism. A systematic review. CNS Neurosci Ther. 2019 Feb.; 25(2):159-174.

Nakagawa O, Fujisawa K, Ishizaki T, Saito Y, Nakao K, Narumiya S. ROCK-I and ROCK-II, two isoforms of Rho-associated coiled-coil forming protein serine/threonine kinase in mice. FEBS Lett. 1996 Aug. 26; 392(2):189-93.

Novak P, Kontsekova E, Zilka N, Novak M. Ten years of tau-targeted immunotherapy: the path walked and the roads ahead. *Front Neurosci.* 2018; 12:798.

Panza F, Lozupone M, Seripa D, et al. Development of disease-modifying drugs for frontotemporal dementia spectrum disorders. *Nat Rev Neurol.* 2020; 16(4):213-228.

Saijo E, et al. 4-repeat tau seeds and templating subtypes as brain and CSF biomarkers of frontotemporal lobar degeneration. Acta Neuropathologica DOI: 10.1007/s00401-019-02080-2 (2019).

Shibuya M, Asano T, Sasaki Y. Effect of fasudil HCl, a protein kinase inhibitor, on cerebral vasospasm. *Acta Neurochir Suppl.* 2001; 77:201-4.

Stamelou M, Reuss A, Pilatus U, Magerkurth J, Niklowitz P, Eggert K M, Krisp A, Menke T, Schade-Brittinger C, Oertel W H, Höglinger G U. Short-term effects of coenzyme Q10 in progressive supranuclear palsy: a randomized, placebo-controlled trial. Mov Disord. 2008 May 15; 23(7):942-949.

Tolosa E, Litvan I, Höglinger G U, Burn D, Lees A, Andres M V, Gomez-Carrillo B, Leon T, Del Ser T; TAUROS Investigators. A phase 2 trial of the GSK-3 inhibitor tideglusib in progressive supranuclear palsy. Mov Disord. 2014 April; 29(4):470-8.

Uehata M, Ishizaki T, Satoh H, Ono T, Kawahara T, Morishita T, Tamakawa H, Yamagami K, Inui J, Maekawa M, Narumiya S. Calcium sensitization of smooth muscle mediated by a Rho-associated protein kinase in hypertension. Nature. 1997 Oct. 30; 389(6654):990-4.

VandeVrede L, Dale M L, Fields S, Frank M, Hare E, Heuer H W, Keith K, Koestler M, Ljubenkov P A, McDermott D, Ohanesian N, Richards J, Rojas J C, Thijssen E H, Walsh C, Wang P, Wolf A, Quinn J F, Tsai R, Boxer A L. Open-Label Phase 1 Futility Studies of Salsalate and Young Plasma in Progressive Supranuclear Palsy. Mov Disord Clin Pract. 2020 Apr. 10; 7(4):440-447.

Yamaguchi H, Kasa M, Amano M, Kaibuchi K, Hakoshima T. Molecular mechanism for the regulation of rho-kinase by dimerization and its inhibition by fasudil. Structure. 2006 Mar.; 14(3):589-600.

Yanamandra K, Kfoury N, Jiang H, et al. Anti-tau antibodies that block tau aggregate seeding in vitro markedly decrease pathology and improve cognition in vivo. Neuron. 2013; 80(2):402-414.

Zalewski N, Botha H, Whitwell J L, Lowe V, Dickson D W, Josephs K A. FDG-PET in pathologically confirmed spontaneous 4R-tauopathy variants. J Neurol 2014; 261: 710-716.

Zhang W, Tarutani A, Newel K L, Murzin A G, Matsubara T, Falcon B, Vidal R, Garringer H J, Shi Y, Ikeuchi T, Murayama S, Ghetti B, hasegawa M, Goedert M, Scheres S H W, Novel tau filament fold in corticobasal degeneration. Nature. 2020; 580: 283-287.

The disclosure of each reference set forth herein is incorporated herein by reference in its entirety.

The invention claimed is:

1. A method of treating a patient clinically diagnosed with probable progressive supranuclear palsy or corticobasal syndrome, comprising administering a therapeutically effective amount of fasudil, hydroxyfasudil (M3), or a salt thereof, to said patient.

2. The method according to claim 1 wherein the patient is clinically diagnosed with probable progressive supranuclear palsy with Richardson syndrome or corticobasal syndrome with probable sporadic corticobasal degeneration.

3. The method according to claim 1 where said treatment continues for at least 6 months.

4. The method according to claim 1, wherein said fasudil or hydroxyfasudil (M3) or salt thereof is administered in a dose of at least 70 mg per day.

5. The method according to claim 4, wherein said dose is administered in three equal portions throughout the day.

6. The method according to claim 5, wherein the total daily dose is between 70 mg and 240 mg.

7. The method according to claim 4, wherein the total daily dose is administered in a sustained release formulation.

8. The method according to claim 6, wherein the total daily dose is between 180 mg and 240 mg.

9. The method according to claim 1, wherein fasudil or a salt thereof is administered to the patient.

10. The method according to claim 4, wherein fasudil or a salt thereof is administered to the patient.

11. The method according to claim 6, wherein fasudil or a salt thereof is administered to the patient.

12. The method according to claim 1, wherein the patient is clinically diagnosed with probable progressive supranuclear palsy.

13. The method according to claim 1, wherein the patient is clinically diagnosed with probable corticobasal syndrome.

14. The method according to claim 9, wherein the fasudil is fasudil hydrochloride hemihydrate.

15. The method according to claim 6, wherein the fasudil is fasudil hydrochloride hemihydrate.

16. A method of treating a patient clinically diagnosed with probably progressive supranuclear palsy or corticobasal syndrome, comprising administering a therapeutically effective amount of fasudil or a salt thereof to said patient at a dose between 70 mg and 240 mg per day.

17. The method according to claim 16, wherein the fasudil is fasudil hydrochloride hemihydrate.

18. The method according to claim 16, wherein the fasudil or a salt thereof is administered in a dose of between 180 mg and 240 mg.

\* \* \* \* \*